United States Patent [19]

Drauschke et al.

[11] Patent Number: 5,091,158
[45] Date of Patent: Feb. 25, 1992

[54] AUTOCLAVE FOR STERILIZING WASTE USING AN AIR-LOCK

[75] Inventors: Stefan Drauschke; Michaela Birkholz, both of Berlin, Fed. Rep. of Germany

[73] Assignee: K-E-G Krankenhaus-Entsorgungs Gesellschaft m.b.H., Berlin, Fed. Rep. of Germany

[21] Appl. No.: 445,785

[22] Filed: Dec. 4, 1989

[30] Foreign Application Priority Data

Dec. 2, 1988 [DE] Fed. Rep. of Germany ....... 3841076

[51] Int. Cl.$^5$ .................... A61L 2/08; A61L 11/00; A61L 2/04; A61L 2/06
[52] U.S. Cl. .................... 422/295; 422/26; 422/302
[58] Field of Search ............... 422/295, 296, 297, 26, 422/302

[56] References Cited

U.S. PATENT DOCUMENTS

| | | |
|---|---|---|
| 3,606,997 | 9/1971 | Guckel .................. 422/302 |
| 3,994,685 | 11/1976 | Lödige et al. ............ 422/295 |
| 4,927,653 | 5/1990 | Manvell ................. 426/399 |

Primary Examiner—David M. Naff
Assistant Examiner—Timothy J. Reardon
Attorney, Agent, or Firm—Basile and Hanlon

[57] ABSTRACT

An autoclave for sterilizing waste or the like has a stirrer and a loading opening. The loading opening is connected to a pressure lock, which has at least one filling opening to be closed in pressure-tight manner. The filling opening leads into at least one chamber provided in the pressure lock casing. This chamber forms part of a mechanism moving the chamber from a filling position connected to at least one filling opening into a loading position connected to the loading opening.

15 Claims, 1 Drawing Sheet

AUTOCLAVE FOR STERILIZING WASTE USING AN AIR-LOCK

BACKGROUND OF THE INVENTION

1. Field of the Invention

The invention relates to a steam sterilizer or autoclave for sterilizing waste.

2. Description of the Relevant Art

In general, special incinerators are used for disinfecting and sterilizing infectious waste or for destroying organisms. These incinerators suffer from generally known disadvantages, e.g. the environment suffers through emissions in the form of toxic substances in waste gases and possibly unpleasant odors from burning waste and from the support fire. The latter can only be obtained with a considerable energy expenditure and, in the case of the generally used discontinuous installations, the burning of hospital waste which cannot be dispatched for garbage disposal can only occur when the installation has been already adequately heated and therefore thermal energy has been supplied thereto. In addition, in such cases the waste must be intermediately stored.

Autoclaves have already been proposed, but they have not been used, because conventionally a stirrer is provided in the autoclave for size reduction purposes. Consequently, there is a risk that parts of the waste will pass from the interior of the autoclave via the charging or loading opening to the outside, so that there is an increased risk of infection.

The object of the invention is therefore to provide an autoclave making it possible to destroy waste, particularly infectious waste, such as hospital waste. It is a further object to enable this sterilization to take place in an economic manner and with completely satisfactory hygienic loading.

SUMMARY OF THE INVENTION

The invention comprises an autoclave for sterilizing waste or the like. The autoclave has a stirrer and a loading opening. Due to the fact that the loading opening is connected to a pressure lock leading into at least one chamber located in the lock casing, and that the chamber forms part of an apparatus moving the chamber from a filling position connected to at least one filling opening into a loading position connected to the loading opening, the loading apparatus forms part of the autoclave. This means that the loading apparatus is sterilizable, so that the autoclaves can be loaded in a completely satisfactory hygienic manner without it being possible for solid fragments, water, etc., to be jetted out of the autoclave. This measure provides the possibility of using largearea autoclaves for the disposal of infectious material, such as hospital waste, which leads to important economic advantages.

Advantageous further developments and improvements are possible. Through the provision of a turning mechanism as part of the pressure lock, in which are arranged one or more chambers, the complete loading apparatus can be constructed in a relatively simple and space-saving manner.

BRIEF DESCRIPTION OF THE DRAWINGS

Further features and advantages will become apparent by reference to the following detailed description and drawings, wherein.

DESCRIPTION OF THE PREFERRED EMBODIMENT

Figure 1:
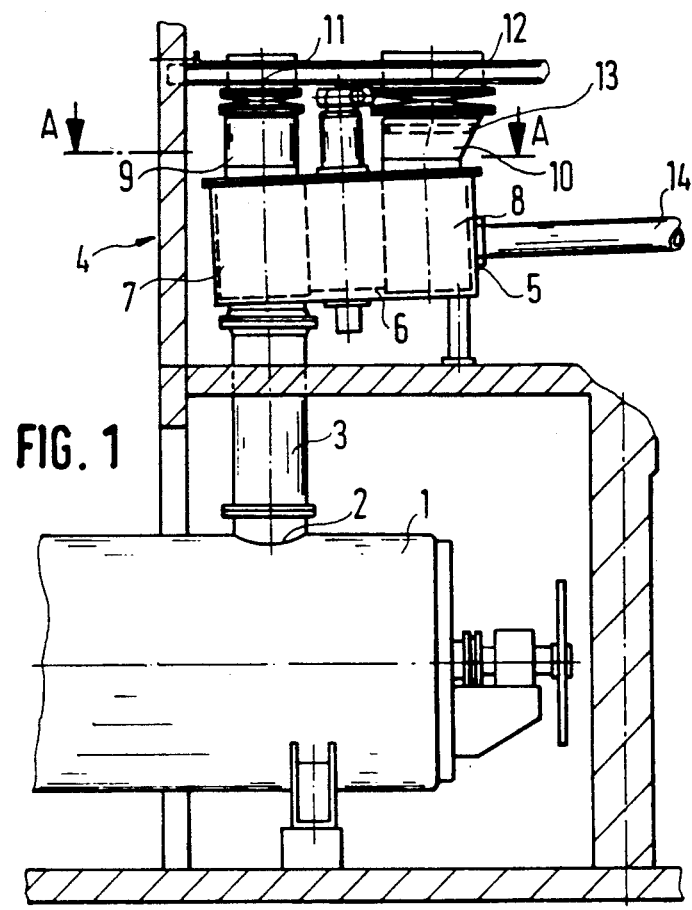
FIG. 1 is a side view of part of the autoclave, showing the loading apparatus.
Figure 2:
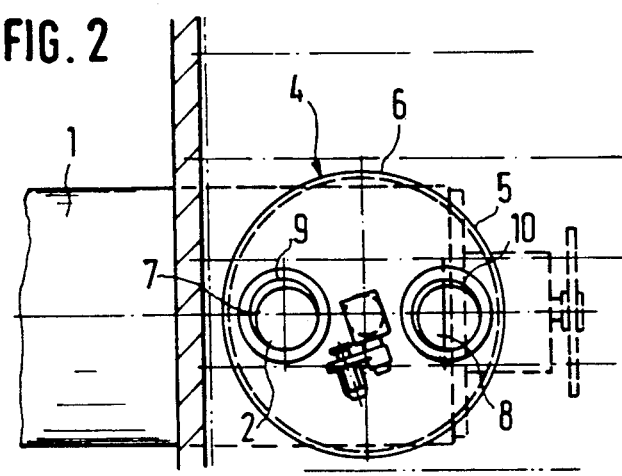
FIG. 2 is a plan view along section line A—A in FIG. 1.

FIG. 1 shows a sterilizer or autoclave 1, which is conventionally equipped with stirrers in order to homogenize, heat and circulate the waste or the like which is to be sterilized. For the sterilization of its contents, process steam is made to act on the autoclave 1. Autoclave 1 is provided with a charging or loading opening 2, which is connected to a tubular or funnel-shaped charging or loading channel or shaft 3. Loading channel 3 forms part of a loading or charging apparatus or pressure lock 4. Loading apparatus 4 has a cylindrical casing 5, in which is mounted a turning mechanism 6 or disk movable about the central point. A plurality of chambers 7, 8 are arranged in circular manner around the circumference of the turning mechanism 6. Only two chambers are visible and are intended to receive infectious and/or wet organic materials in containers. The chambers 7, 8 are terminated towards the bottom, e.g. by a slide 15, which is opened on turning into the position in which one chamber 7, 8 is located above the loading channel 3, so that the particular chamber is emptied into the autoclave 1. The chambers 7, 8 can also be open to the bottom, but then the containers rub against the base of the casing. It is also conceivable for there to be only one closure above the loading channel 3. The loading apparatus 4 has two diametrically facing filling openings 9, 10, which issue into an underlying chamber 7, 8. In the preferred embodiment, there is a filling opening 9 in the extension of the loading channel 3 and the chamber 7 positioned above it. The filling openings 9, 10 are sealed in pressure-tight manner by means of closures, 11 and 12 which can be constructed as slides. The turning mechanism 6 is driven by means of an electric drive 16 and a corresponding transmission means (not shown). A variable-speed gear (not shown) is provided, enabling the speed of the disk or turning mechanism 6 to be adjusted.

The casing 5 and the turning mechanism 6 of the loading apparatus 4 are inclined somewhat towards the loading channel 3, so that condensate can flow out.

It is possible to provide cleaning nozzles 13 or the like in the filling openings 9, 10 and optionally also in the chambers 7, 8 and/or the loading channel 3. For example it is possible to integrate into the filling opening 10 a nozzle ring 13 through which the cleaning liquid is supplied, which flows through and cleans the loading apparatus and then flows out into the autoclave 1. Simultaneously the nozzle ring 13 can be used for flushing out and cleaning a replacement container inverted over the filling opening 10 following the emptying thereof. If a replacement container is used, the infectious and/or wet organic waste is filled into bags and transported into the replacement container.

Preferably the casing 5 is connected to an air or gas suction tube 14 by means of which the air or gas is sucked off, so that during filling it cannot pass to the outside. The air sucked off by means of suction tube 14 is cleaned by means of a bacterial filter (not shown).

For filling the chambers 7, 8 and loading the autoclave 1, the pressure-tight closures 11, 12 are opened. The pressure-tight closure 12 is opened and the chamber 8 is filled with infectious and/or wet organic materials, or the container is supplied directly to the autoclave 1 via filling opening 11, the underlying chamber 7 and the loading channel 3. The turning mechanism 6 continues to turn, so that another chamber is located below the filling opening 12 or 11, so that filling can be repeated. When a filled chamber 7, 8 has been turned into the loading position over the loading channel, opening takes place when slides 15 or the like at the bottom of the chamber are turned, so that it is completely open towards the bottom when aligned with the loading channel 3. The containers drop vertically into the autoclave and are taken up by the stirrer. No infectious or wet organic material or water can be jetted to the outside, because the loading apparatus 4 holds them back. Any matter which may be adhering within the loading channel 3 or elsewhere can be removed by the cleaning nozzles 13. The closures 11, 12 are closed in pressure-tight manner for sterilization both of the material in the autoclave 1 and also the loading apparatus 4 and the complete system is disinfected or sterilized with the process steam and subsequently loading can be resumed. The loading apparatus 4 constructed as a pressure lock, and the autoclave 1 are designed for an operating pressure of 4 bar.

The rotation of the turning mechanism 6, whose speed can be controlled, can take place continuously or stepwise at intervals.

In the preferred embodiment, the loading apparatus 4 is constructed as a turning mechanism. However, it is also conceivable to provide a shifting means. Then the chambers are longitudinally juxtaposed and the shifting movement takes place in a translatory manner.

It is to be understood that the foregoing description is to be considered exemplary rather than limiting, and the true scope of the invention is that defined in the following claims.

What is claimed is:

1. In an autoclave for sterilizing waste having a stirrer and a vertically extending loading opening, the improvement comprising:
a horizontally disposed pressure lock connected to the vertically extending loading opening, the pressure lock having a casing enclosing a horizontally moveable member, the casing having at least one vertically extending filling opening defined therein, and closure means disposed at the top of each of said filling openings for sealing said filling opening in a pressure-tight manner, the casing and the moveable member defining at least one chamber moveable between a filling position and a loading position, and means for selectively moving the chamber between the filling position, wherein the chamber is in communication with the filling opening and isolated from the loading opening, and the loading position wherein the chamber is in communication with the loading opening and isolated from the filling opening.

2. The autoclave as defined in claim 1 wherein the moveable member comprises a cylindrical disk rotatable about an axis of rotation, wherein each of said at least one chamber includes a generally cylindrical aperture formed in the disk having a longitudinal axis generally parallel to and offset from the axis of rotation.

3. The autoclave as defined in claim 1, wherein the moveable member comprises a disk.

4. The autoclave as defined in claim 1, wherein the moveable member has a plurality of chambers.

5. The autoclave as defined in claim 1, further comprising means for closing the chamber, wherein the chamber closing means is disposed adjacent a bottom of the chamber and is closed in the filling position and opens on moving into the loading position.

6. The autoclave as defined in claim 1, further comprising a loading channel between the chamber and the loading opening.

7. The autoclave as defined in claim 6, further comprising means, integral with the pressure lock, for cleaning the pressure lock and the autoclave.

8. The autoclave as defined in claim 7 wherein the cleaning means comprises a cleaning nozzle disposed within the filling opening.

9. The autoclave as defined in claim 7 wherein the cleaning means comprises a cleaning nozzle disposed within the chamber.

10. The autoclave as defined in claim 7 wherein the cleaning means comprises a cleaning nozzle disposed within the loading channel.

11. The autoclave as defined in claim 1, further comprising an additional filling opening located in the casing generally coaxial with the loading opening and the chamber when the chamber is in the loading position.

12. The autoclave as defined in claim 1, wherein the selective moving means comprises an electric drive connected to the moveable member for moving the chamber into different predefined positions.

13. The autoclave as defined in claim 1, further comprising means, connected to the pressure lock, for suctioning air and gas.

14. An autoclave for sterilizing waste comprising:
a large autoclave vessel for receiving a plurality of smaller waste charges from a loading opening for sterilization, said loading opening having a vertically extending longitudinal axis to receive waste charges by gravitational forces;
a stirrer disposed within said autoclave vessel for mixing said smaller waste charges received within said autoclave vessel during sterilization; and
a pressure lock for sealing said loading opening to prevent an interior of said autoclave vessel from directly opening to atmosphere, said pressure lock connected to said loading opening and having a casing enclosing a moveable member, said moveable member capable of movement in a horizontal plane normal to said vertically extending longitudinal axis of said loading opening, said casing having at least one vertically extending filling opening defined therein offset from said loading opening, and closure means disposed at the top of each of said filling openings for sealing said filling opening in a pressure-tight manner, said casing and said moveable member defining at least one chamber moveable horizontally between a filling position, wherein said chamber is in communication with said filling opening and isolated from said loading opening, and a loading position, wherein said chamber is in communication with said loading opening and isolated from said filling opening, and means for selectively moving said at least one chamber between said filling position and said loading position.

15. The autoclave of claim 14, further comprising:
a slide disposed in a bottom of each of said at least one chamber, said slide openable on turning into said loading position to empty said at least one chamber into said autoclave vessel, said slide for preventing said waste from rubbing against said casing.

* * * * *